United States Patent [19]
Szabo

[11] Patent Number: 5,376,265
[45] Date of Patent: Dec. 27, 1994

[54] OZONE/WATER CONTACTOR

[76] Inventor: Louis Szabo, 2940 Olafson Avenue, Richmond, B.C., Canada, V6X 2R3

[21] Appl. No.: 189,645

[22] Filed: Feb. 1, 1994

[51] Int. Cl.$^5$ .................................................. C02F 1/78
[52] U.S. Cl. ........................... 210/188; 210/192; 210/205; 210/218; 210/220; 210/760; 210/120
[58] Field of Search .......... 210/150, 760, 764, 188, 210/151, 192, 205, 218, 220, 120; 366/336, 338, 339, 340; 138/41, 42

[56] References Cited

U.S. PATENT DOCUMENTS

| | | | |
|---|---|---|---|
| 1,853,045 | 4/1932 | Gnau | 261/77 |
| 2,009,230 | 7/1935 | Hartmann | 210/760 |
| 2,050,771 | 8/1956 | Wait | 210/760 |
| 3,421,625 | 1/1969 | Fritz | 210/188 |
| 3,448,045 | 6/1969 | Hess et al. | 210/760 |
| 3,674,216 | 7/1972 | Blair | 210/760 |
| 3,704,006 | 11/1972 | Grout | 259/4 |
| 3,732,163 | 5/1973 | Lapidot | 210/760 |
| 3,823,728 | 7/1974 | Burris | 210/760 |
| 3,865,352 | 2/1975 | Nelson et al. | 366/352 |
| 4,029,578 | 6/1977 | Turk | 210/760 |
| 4,061,313 | 12/1977 | Brauner et al. | 366/340 |
| 4,121,906 | 10/1978 | Oldham et al. | 366/336 |
| 4,136,976 | 1/1979 | Leffelman | 366/336 |
| 4,176,061 | 11/1979 | Stopka | 210/760 |
| 4,204,775 | 5/1980 | Speer | 366/336 |
| 4,252,654 | 2/1981 | Leitzke et al. | 210/760 |
| 4,255,257 | 3/1981 | Greiner et al. | 210/760 |
| 4,256,574 | 3/1981 | Bhagava | 210/760 |
| 4,430,306 | 2/1984 | Namba et al. | 210/760 |
| 4,537,684 | 8/1985 | Gallup et al. | 210/696 |
| 4,622,151 | 11/1986 | Hiltebrand et al. | 210/760 |
| 4,752,383 | 6/1988 | McKay et al. | 210/221.2 |
| 4,780,287 | 10/1988 | Zeff et al. | 422/186.3 |
| 5,015,394 | 5/1991 | McEllhenney et al. | 210/760 |
| 5,141,636 | 8/1992 | Flanagan et al. | 210/748 |
| 5,141,717 | 8/1992 | McRae | 210/746 |
| 5,207,993 | 5/1993 | Burris | 210/188 |
| 5,213,773 | 5/1993 | Burris | 210/188 |
| 5,240,598 | 8/1993 | Portier et al. | 210/151 |
| 5,249,688 | 10/1993 | Hwang | 209/170 |
| 5,269,922 | 12/1993 | Lin | 210/286 |
| 5,302,298 | 4/1994 | Leitzke | 210/188 |
| 5,314,644 | 5/1994 | Michelsen et al. | 261/84 |

Primary Examiner—Cynthia L. Nessler
Attorney, Agent, or Firm—Adrian Zahl

[57] ABSTRACT

An gas/fluid contactor is provided for reacting water and other fluids with an ozone-containing gas. The contactor comprises an elongate tubular reaction chamber having a gas/fluid combining chamber adjacent the inlet to draw an ozone-containing gas into the device and to provide an initial mixing between the gas and the fluid. One or more mixing chambers are positioned within the reaction chamber, each being filled with a material that provides a matrix of solid elements with interstices of between 0.1 and 2.0 mm. in diameter between the solid elements.

4 Claims, 1 Drawing Sheet

OZONE/WATER CONTACTOR

FIELD OF THE INVENTION

The present invention relates to a device for reacting an ozonated gas with a contaminated fluid, in particular water, for decontamination of the fluid by the antimicrobial action of the ozone.

BACKGROUND OF THE INVENTION

Water purification systems that take advantage of the germicidal properties of ozone enjoy a variety of uses, including the purification of effluent from industrial processes and portable facilities, such as are found on boats, as well as the sterilization of circulating water in hot tubs and swimming pools. Such systems typically comprise an ozone-producing apparatus and an ozone/water reactor, or contactor. The ozone-producing apparatus typically comprises an air chamber, within which an ultraviolet ("UV") lamp is positioned. An air stream flows past the UV lamp, with the lamp's radiation converting a portion of the oxygen in the air to ozone. The ozonated air is then channelled to the contactor for reaction with the contaminated water. The spent ozonated air may be collected for recirculation within the system.

The contactor is faced with several requirements and limitations. The essential requirement of a contactor is that it thoroughly combine the ozonated air with the contaminated fluid. Various means have been proposed to achieve this. For example, U.S. Pat. No. 2,009,230 (Hartman) discloses a long helical tube with ozonated air and contaminated water being introduced into one end, and the other end discharging into a secondary reaction chamber. Other devices have utilized a reaction chamber within which the ozonated air and the fluid are stirred, as in U.S. Pat. No. 4,728,441 (King), or wherein the reaction chamber simply comprises a tank into which the ozone and contaminated fluid are introduced at one end and removed from the other end, for example as disclosed in U.S. Pat. No. 4,256,574 (Bhargava). In general, a more complete reaction of the ozone and fluid is possible where the reaction chamber is elongate, such as a long tube, with the reactants being introduced at one end and withdrawn from the other end on a continuous basis. In contrast, a reaction chamber comprising a tank is better suited to batch processing of reactants; this approach is not in general well suited to the requirements of an ozone contactor.

Where the reaction chamber consists of a long tubular chamber, which may total 18 feet or more in length, the tube should preferably be coiled or otherwise configured to be relatively compact.

In order to thoroughly combine the ozone and contaminated fluid, it is not sufficient to merely bubble the ozone through the fluid. There must be provided additional means to thoroughly combine the water and ozonated air. The use of a stirring paddle, as disclosed in King, is applicable for use with a relatively large reaction chamber, but not in a compact tube-type contactor. Accordingly, it is desirable to provide means to thoroughly combine the reactants within a tubular reaction chamber. This may be accomplished by providing means to finely divide the ozonated gas as it flows through the chamber, for example by passing it through a fine mesh or a bed of granular material.

SUMMARY OF THE INVENTION

The present invention is an ozonated gas/fluid contactor intended for use in a decontamination system for water and other fluids. The contactor comprises an elongate tubular reaction chamber, which preferably comprises a helical coil, having an inlet and outlet at its first and second ends, respectively, and a gas/fluid combining chamber adjacent the inlet to draw an ozone-containing gas into the device and to provide an initial mixing between the gas and the fluid. The combining chamber preferably comprises an elongate chamber having a restricted portion therein for the creation of a venturi effect as a stream of fluid flows through the chamber. A gas inlet enters the combining chamber at the restricted portion, and the venturi effect created at the restricted portion serves to draw the ozonated gas into the combining chamber and conduct an initial mixing of the fluid and gas. One or more mixing chambers are positioned within the reaction chamber. Each mixing chamber is filled with a material that provides a matrix, having solid elements with interstices of between 0.1 and 2.0 mm. in diameter between the solid elements. The matrix may consist of a bed of crushed glass, wherein the particle size is generally between 0.5 and 2.0 mm.

The fluid and gas mixture exits the reaction chamber at its outlet, and there may be provided an off-gas collector at or adjacent the outlet. The collector comprises a chamber having an aperture at its lower end communicating with the outlet of the reaction chamber. A float, with a valve body at its upper end, is positioned within the chamber, the valve body cooperating with a valve housing to selectively block the opening of an exit conduit leading from the chamber. The valve body and housing may comprise a needle valve. The exit conduit may be linked to an ozone generator, in order to recycle the spent ozonated air within the decontamination system. A portion of the water exiting the tube first enters the collector, and therein releases the spent ozonated air. As the gas is released, the water level within the chamber drops, causing the valve body to retract from the mouth of the valve housing to allow the gasses to escape.

The length of the tube is preferably selected to provide optimal contact time between the ozonated air and the water. In practice, for most applications, this length is about 18 feet. Preferably, the tube is coiled for space savings.

DETAILED DESCRIPTION OF THE PREFERRED EMBODIMENT

Figure 1:
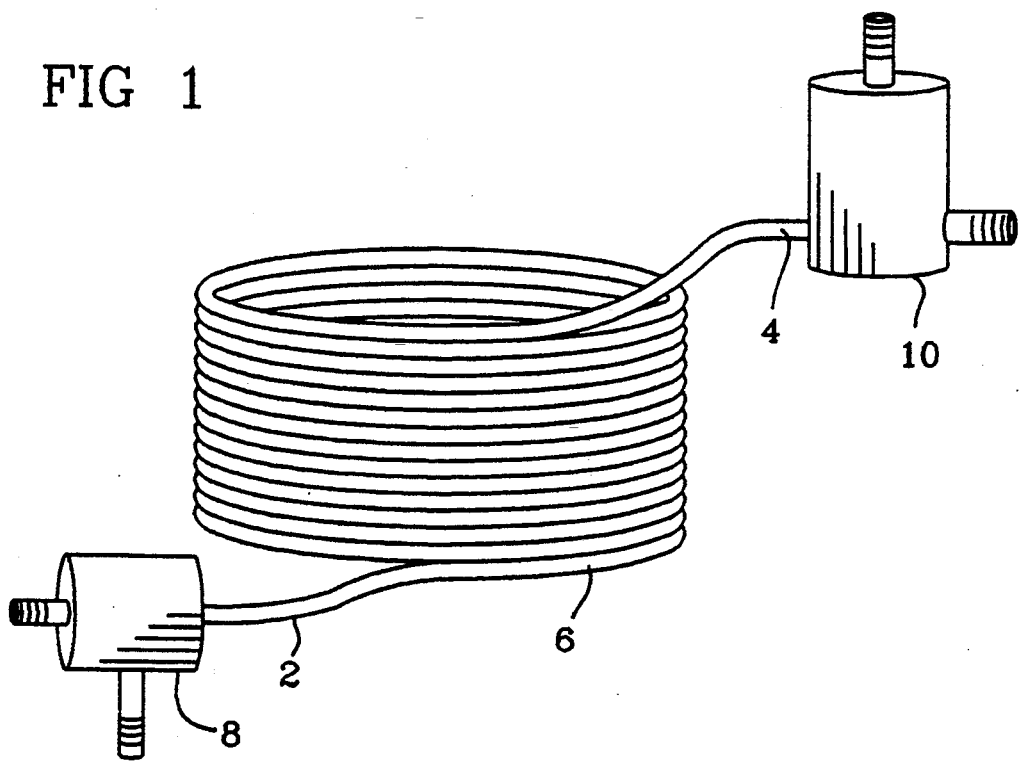
FIG. 1 is a perspective view of a contactor according to the present invention.

Referring to FIG. 1, the present invention includes a reaction chamber, comprising a stainless steel tube with a length of about 18 feet. The tube has straight inlet and outlet portions 2, 4 and a helically coiled body 6. The inlet portion 2 extends from a primary mixer, described below, that relies on a venturi effect generated by the fluid flowing therethrough to draw a stream of ozonated air into the fluid stream. The outlet portion 4 is linked to an off-gas collector 10, described below. The body 6 is coiled into a helix, for space saving.

Figure 2:
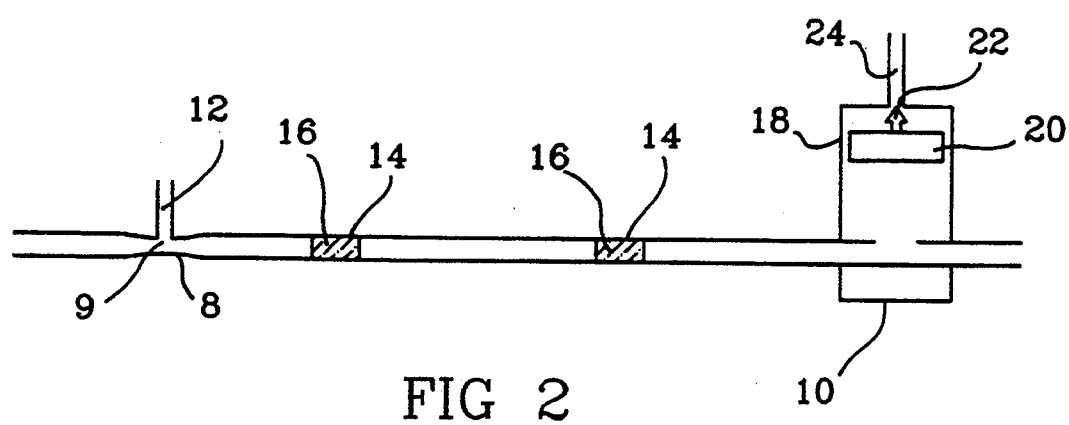
FIG. 2 is a schematic view, in section, of the interior of the contactor.

Turning to FIG. 2, the primary mixer 8 comprises a chamber wherein incoming fluid is channelled through a restricted portion 9 and is there combined with an incoming stream of ozonated gas entering the chamber through a nozzle 12. The narrowing of the fluid flow within the chamber generates a venturi effect that draws the gas into the chamber. The suction created by the venturi draws through an ozone generator, not shown, that feeds ozonated gas to the nozzle 12. The combining chamber provides as well an initial mixing of the fluid and gas.

Within the interior of the body 6 of the reaction chamber, there are provided several mixing chambers 14. Preferably, at least two such chambers are provided, with a first chamber being positioned close to the inlet portion of the reaction chamber, and a second chamber intermediate the inlet and outlet portions. The mixing chambers each comprise a matrix of solid elements having relatively small interstices, i.e. between 0.1 and 2.0 mm., between the solid elements. The matrix serves to finely divide any gas bubbles flowing through the mixing chambers, in order to increase the surface area of the ozonated gas exposed to the contaminated fluid within the contactor. While any fine matrix will serve this purpose, including a simple mesh screen, the preferred embodiment employs a bed of finely divided glass particles. Each mixing chamber 14 comprises a mesh sleeve 1, closed at its ends, positioned within the tube and filled with finely divided crushed glass 18 having a particle diameter of generally between 0.5 and 2.0 mm. The water and gas mixture flowing through the bed becomes finely divided and thoroughly mixed as it encounters the glass particles.

The off-gas collector comprises a fully enclosed housing 18 having an aperture therein for the inflow of water/gas mixture from the outlet portion 4. The ozone within the ozonated air will by this point have reacted with the water, and will have largely been reconverted to bivalent oxygen. However, the air will contain residual ozone, and possibly other contaminants absorbed from the water, and it is desirable to prevent the release of this contaminated air into the atmosphere. Accordingly, the collector may be linked to the ozone generator within the system, in order to recycle the air within the system.

The decontaminated water, with fine bubbles of spent gas suspended therein, exits the reaction chamber and accumulates within the housing 18, and causes a float 20 positioned within the housing to rise. The float 20 is provided with a generally conical valve body 22 at its upper end, adapted to mate with an aperture 24 within the roof of the housing. The aperture 24 comprises a valve housing, that in combination with the valve body comprises a needle valve that selectively blocks the outflow of spent gas. The valve body 22 blocks the aperture when the water level within the housing reaches a predetermined level, preventing the escape of gas from the housing. As entrapped gas is released from the water/gas mixture within the housing, the rising gas pressure causes the fluid level to drop and the needle valve to open, allowing the gas to vent from the collector. The released gas is preferably recirculated within the decontamination system by being returned to the ozone generator for the further production of ozonated air. A conduit, not shown, channels the spent gas from the housing to the ozone generator. The housing is further provided with a nozzle for the discharge of purified water, which may then be filtered and either released or further treated within the system.

It will be understood that the embodiment described herein requires the provision of various valves, conduits, controllers, pumps and the like, the arrangement of which would be obvious to one skilled in the art.

While the present invention has been described by way of preferred embodiments thereof, it will be seen that variations may be made thereto, without departing from the spirit and scope of the invention, as described in the appended claims.

I claim:

1. A gas/fluid contactor comprising a first chamber having combining means for combining separate streams of an ozonated gas and a fluid, a second chamber having dispersion means for dispersing said gas within said fluid, a third chamber comprising an off-gas collector, conduits linking said first, second and third chambers, and entry and exit nozzles respectively directing said fluid and said gas into and away from said contactor, said second chamber comprising an elongate helical tube having at least two diffusers therein, a first of said at least two diffusers being positioned adjacent a first end of said helical tube, a second of said at least two diffusers being positioned partway along said helical tube, each of said at least two diffusers comprising a matrix spanning said second chamber, said matrix comprising a bed of glass particles, said bed having interstitial spaces of generally between 0.1 and 2.0 mm in diameter.

2. A contactor as claimed in claim 1, wherein said glass particles comprise crushed glass.

3. A contactor as claimed in claim 1, wherein each of said at least two diffusers is lined with a mesh for the containment of said glass particles.

4. A contactor as claimed in claim 1, wherein said first chamber comprises an elongate chamber having a restricted portion therein, for the creation of a venturi effect as a stream of fluid flows therethrough, with a conduit entering said chamber at said restricted portion for the entry of gas, said gas being drawn into said fluid at said restricted portion.

* * * * *